United States Patent [19]

Harrison

[11] 4,374,516

[45] Feb. 22, 1983

[54] PLANAR DISC MAGNETIC ELECTRODE

[76] Inventor: William H. Harrison, 23341 Burbank Blvd., Woodland Hills, Calif. 91367

[21] Appl. No.: 236,849

[22] Filed: Feb. 23, 1981

Related U.S. Application Data

[63] Continuation-in-part of Ser. No. 97,485, Nov. 26, 1979, abandoned.

[51] Int. Cl.³ .............................................. A61N 1/40
[52] U.S. Cl. ................................... 128/1.3; 128/804; 219/10.79
[58] Field of Search ................................. 128/1.3–1.5, 128/783, 802, 804; 219/10.79; 336/232

[56] References Cited

U.S. PATENT DOCUMENTS

| | | | |
|---|---|---|---|
| 2,847,651 | 8/1958 | Schamanek | 219/10.79 |
| 2,939,049 | 5/1960 | Blackman | 219/10.79 |
| 3,256,417 | 6/1966 | Merrett | 219/10.79 |
| 3,906,181 | 9/1975 | Hibino et al. | 219/10.79 |

*Primary Examiner*—Lee S. Cohen
*Attorney, Agent, or Firm*—Poms, Smith, Lande & Rose

[57] ABSTRACT

An electrode for use in the treatment of animal tissue by hyperthermia particularly adapted for use in the neck regions wherein a planar field of energy is required so as to concentrate therapeutic energy in the area of a plane passing through the electrode with very little energy available to affect adjacent areas beyond close proximity to the plane of the electrode. In the preferred embodiment the electrode comprises disk segments of a conductive material disposed in overlapped relationship on either side of dielectric material to form conductive annular disks separated by dielectric material so as to be a single self-resonant loop.

4 Claims, 13 Drawing Figures

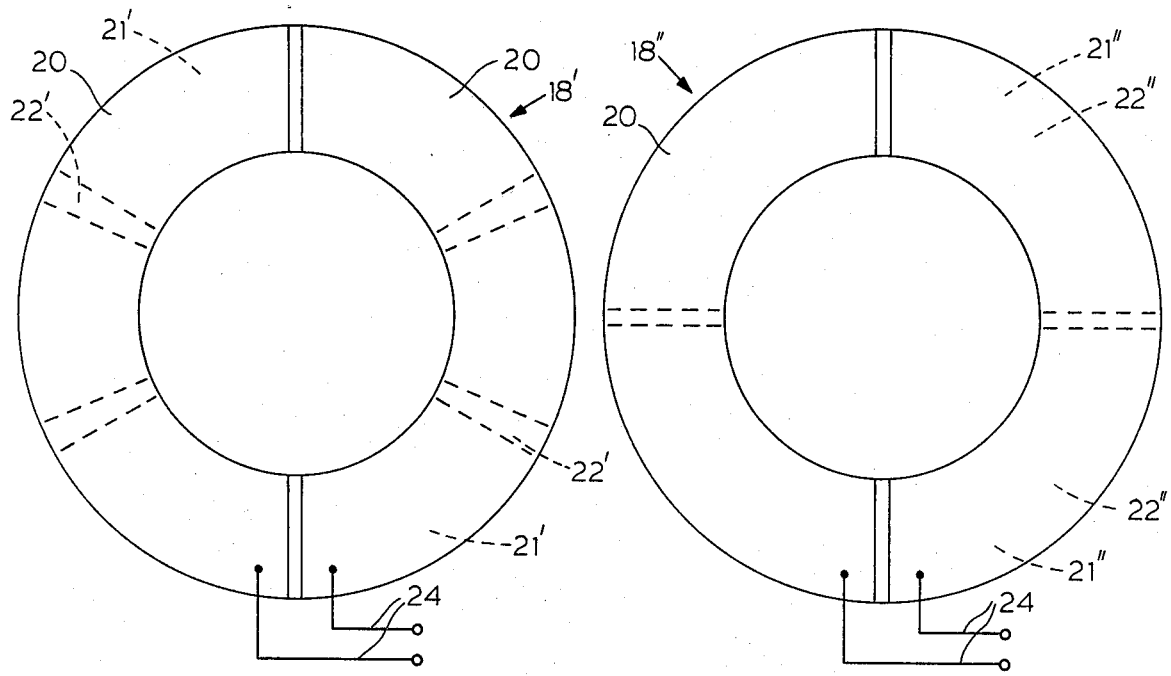
FIG 6
FIG 8
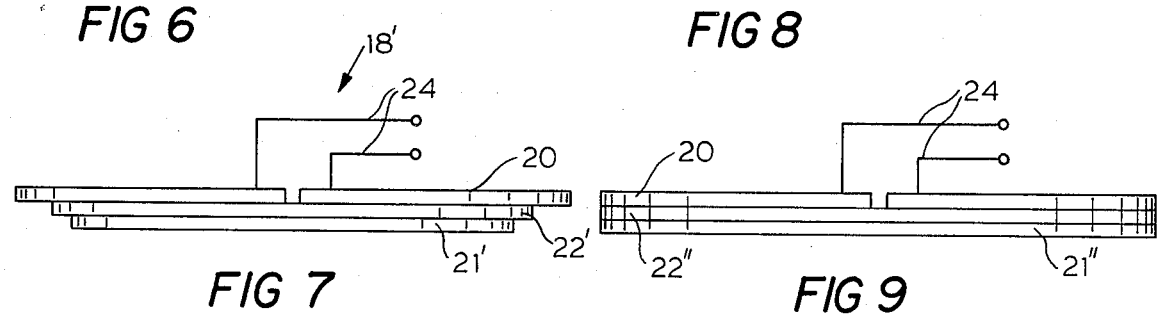
FIG 7
FIG 9
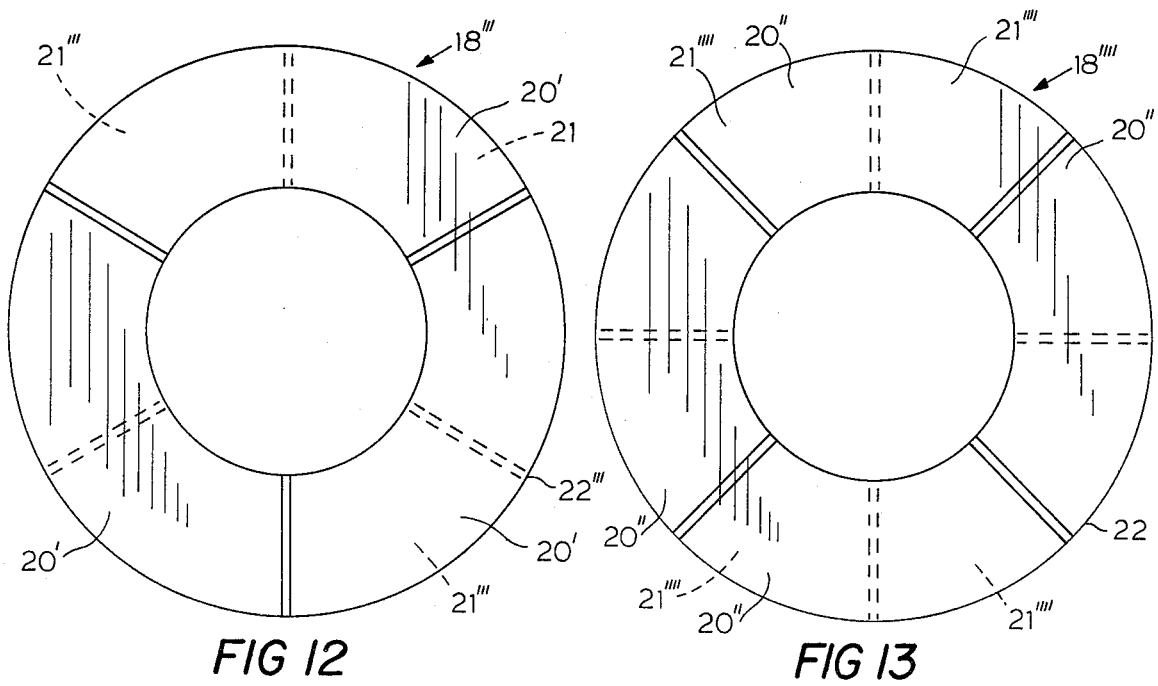
FIG 12
FIG 13

PLANAR DISC MAGNETIC ELECTRODE

BACKGROUND OF THE INVENTION

This is a Continuation-in-part of my prior application Ser. No. 97,485, filed Nov. 26, 1979, now abandoned.

The present invention relates to electrodes used in medical treatment and, more particularly, to electrodes employed with radiofrequency energy to produce deep heating by hyperthermia.

The therapeutic effects of heat have been known for a long period of time. In particular, it has been found that tumors can be heated and, thereby, destroyed. Likewise, it has been known that radiofrequency energy can be employed to cause heating of animal tissue. This has been accomplished by traditional diathermy apparatus.

In my U.S. Pat. No. 4,186,729, an electrode is shown which allows radiofrequency energy to be employed to cause deep heating within an animal body. A simplified drawing of an electrode as disclosed therein is shown in FIG. 1. Prior to my Deep Heating Electrode, a person 10 having a tumor situated deep within his body was virtually unable to have sufficient energy transferred thereto to cause thereapeutic heating of the tumor. Before my invention, such heating could only occur by surgically exposing the tumor and placing traditional diathermy electrodes in electrical contact with opposing surfaces of the tissue to cause the energy to pass therethrough.

According to my invention as disclosed in the above-referenced patent, an electrode 12 in the form of a cylinder, as shown, can be placed about the body of the person 10 over the area of the tumor and deep heating energy transmitted thereto if the electrode 12 is in the form of a single turn self-resonant loop which causes a series of concentric force lines of substantially equal energy to be created inside the cylinder.

The construction of such electrodes is typified by the example of FIG. 2 which appeared as FIG. 8 in the above-referenced patent. In that embodiment, electrode 12 comprises two semi-cylindrical members 14 of an electrically conductive material. Members 14 are disposed in overlapped spaced relationship as shown to form the cylindrical electrode 12. While air can be employed as the dielectric material between the overlapped ends of semi-cylindrical members 14, materials such as plastic can also conveniently be used and the entire assembly bonded together to form a more usable and durable electrode. The area of overlap and the dielectric material are chosen such that when electrode 12 is excited by connecting it to a source of radiofrequency energy as by the leads 16, the inductance of the single turn loop thus formed and the capacitance of the overlapped ends will place the circuit in resonance for maximum energy transfer.

As can be visualized, if the electrode 12 of FIG. 1 with its relatively broad field distribution were used to treat a tumor within the neck of a person 10, it would be impossible to transfer therapeutic energy into the neck without causing energy to also enter the brain itself. Since deep heating energy may have a detrimental effect on the brain, an electrode which produces a narrow field is desired. The potentially toxic effects on the brain can be further evaluated with the present invention when properly positioned.

Because of the required optimum relationship between the inductance (L) and capacitance (C) formed by the cylindrical electrode 12, it is not desireable to merely shorten the height of the cylinder to reduce the side radiations. What is necessary for such treatment is an electrode which will produce a field of energy (and thus the ability to heat) substantially entirely in the immediate area within the center section of the electrode while providing the optimum L/C ratio to minimize voltage build-up which would also produce localized skin and fat heating.

Wherefore, it is the object of the present invention to provide an electrode for use in medical treatment by hyperthermia using the magnetic field approach which electrode concentrates the energy in a plane.

SUMMARY

The foregoing objectives have been met in an electrode for use in the treatment of animal tissue by hyperthermia comprising electrically conductive material disposed to from a single turn self-resonant loop and adapted for coupling to a supply of radiofrequency energy by the improved configuration comprising the electrically conductive material comprising a plurality of planar members being shaped in the form of partial annular disk segments, said members being disposed in overlapping spaced relationship with a dielectric material disposed between the overlapped portions to form an annular disk electrode which is self-resonant.

In the preferred embodiment, this objective is accomplished by an electrode comprising two virtually semi-annular conductive disk members, each having an outside radius of $r_o$ and an inside radius of $r_i$. The two disk members are placed in spaced end-to-end relationship in a common plane. A dielectric material is placed across the two gaps and a second pair of partial-annular conductive disk members, each having an outside radius of $r_o$ and an inside radius of $r_i$, are disposed symetrically across the gaps in contact with the dielectric material.

The arc length of the second pair of disk members is determined by the amount of capacity required to bring the structure to resonance and the capacity per unit length. The maximum arc length occurs when the second conductive disks have an arc length equal to the first (e.g., with the preferred embodiment, when almost equal to 180°). This will most often be the case when the dielectric material thickness has been increased such as for breakdown power considerations, and less capacity per unit length is obtained.

In alternate embodiments, the pair of semi-annular conductive disk members are replaced by a plurality of end-spaced partial-annular members totaling 360°. The gaps are then covered with the dielectric material and second partial-annular members as with the preferred embodiment.

DESCRIPTION OF THE DRAWINGS

FIG. 6 is a plan view of the electrode of the present invention in its preferred embodiment, shown with intermediate gap coverage.

FIG. 7 is an edge view of the electrode of FIG. 6.

FIG. 8 is a plan view of the electrode of the present invention in its preferred embodiment, shown with maximum gap coverage.

FIG. 9 is an edge view of the electrode of FIG. 8.

FIG. 12 is a plan view of the electrode of the present invention in an alternate embodiment.

FIG. 13 is a plan view of the electrode of the present invention in another alternate embodiment.

DESCRIPTION OF THE PREFERRED AND ALTERNATE EMBODIMENTS

Figure 1:
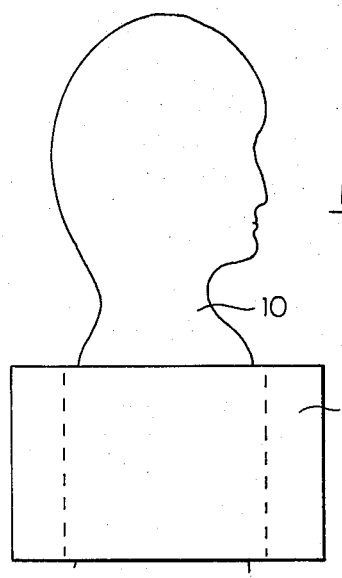
FIG. 1 is a simplified drawing of a prior art electrode disposed for treatment of a human patient.
Figure 2:
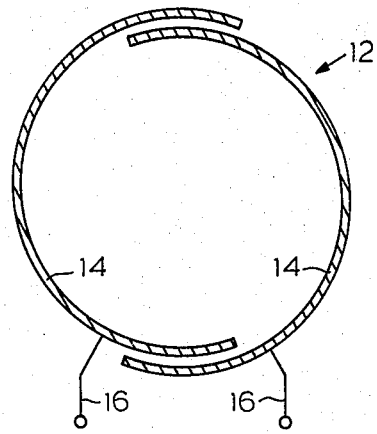
FIG. 2 is a simplified drawing showing a typical construction embodiment for prior art electrodes such as the one of FIG. 1.
Figure 3:
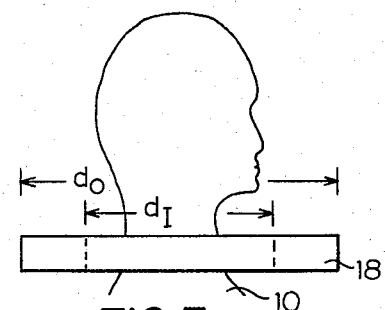
FIG. 3 is a simplified drawing showing the electrode of the present invention positioned for treatment of the neck area of a human patient.

Referring first briefly to FIG. 3, the general configuration of an electrode 18 according to the present invention is shown. Electrode 18 comprises an annular disk having an outside diameter $d_o$ and an inside diameter $d_i$, where the inside diameter $d_i$ is chosen to just allow passage of the electrode 18 over the head of a person 10. Incidentally, such a configuration has also been found to be beneficial in providing localized heating in the shoulder or pelvic region as by passing an arm or leg therethrough.

Figure 4:
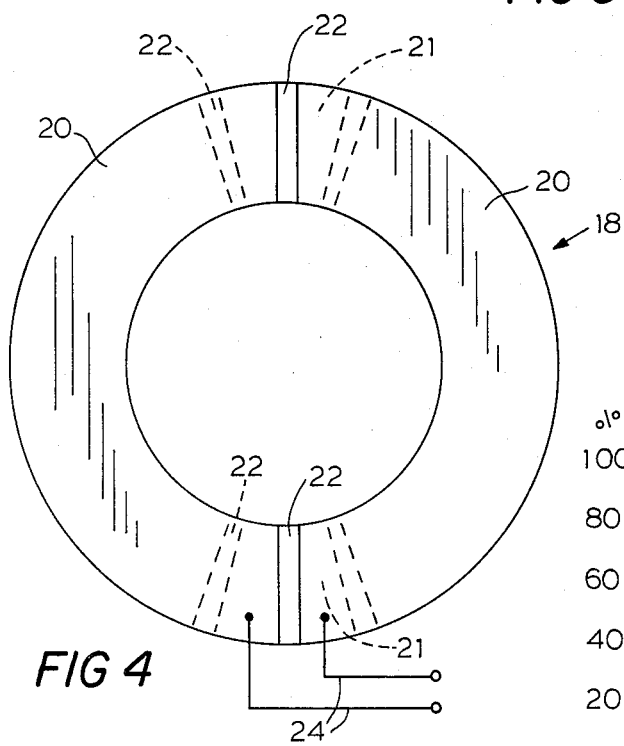
FIG. 4 is a plan view of the electrode of the present invention in its preferred embodiment, shown with minimum gap coverage.
Figure 5:
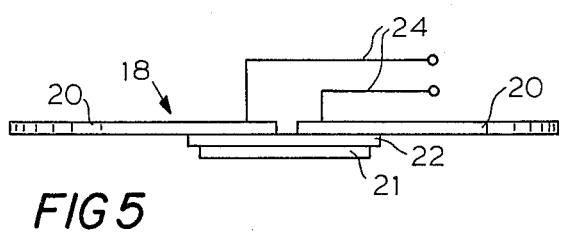
FIG. 5 is an edge view of the electrode of FIG. 4.

Referring next to FIGS. 4 and 5, the electrode 18 is shown in greater detail in one of its embodiments. The electrode 18 is comprised of four partial-annular disk members 20 and 21 of an electrically conductive material such as sheet aluminum. Each member 20, 21, has an inside radius of $d_i/2$ and an outside radius of $d_o/2$. As will be seen from the descriptions of the various embodiments hereinafter, the arc-lengths and number of members 20, 21 will vary, but the principle remains the same.

In the embodiment of FIGS. 4 and 5, members 20 are a pair of virtually semi-annular disks. That is, they are just short of an arc-length of 180°. They are disposed in a common plane in spaced end-to-end relationship to form an annular disk as shown having gaps therein. A dielectric material 22 is placed over the gaps and short arc-length members 21 are then placed symetrically over dielectric material 22 in contact therewith.

This configuration places two capacitors in series across each gap. That is, there are a total of four series capacitors, two at each end of the semi-annular disks 20. As desired, this represents electrically a single turn which can be brought into resonance with the series capacitors. If the inductance is large, i.e., $d_i$ and $d_o$ are large, the amount of capacity required will be small and the required overlap of members 20, 21 will likewise the small. If the dielectric materials 22 is thin, a further reduction in overlap is required.

The balance of construction is very similar to that described in the above-referenced patent. The choices of dielectric material 22 remain the same with polytetrafluourethylene being preferred. The electrode 18 is adapted for connection to a source of radio frequency energy as symbolized by the two electrical leads 24. Any of the methods described in my above-referenced patent can be employed in actual practice. All that is required is that the energy be coupled into the single turn loop.

Figure 10:
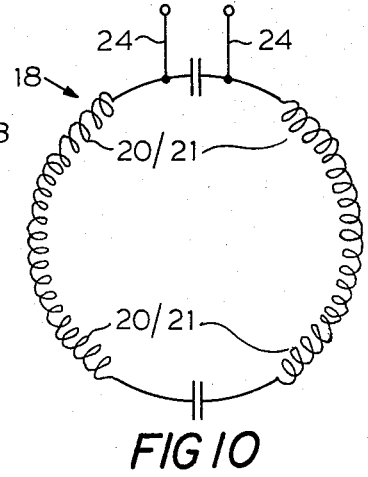
FIG. 10 is a circuit drawing of the equivalent circuit of the electrode of FIGS. 4 through 9.

The equivalent circuit of electrode 18 is shown in FIG. 10. As can be seen, the partial-annular disk members 20, 21 each form a portion of the resultant single turn loop of inductance and the overlapped portions with the dielectric material between forming capacitances. By the proper spacing of the members, choice of dielectric material, and relationship of the outside diameter $d_o$ to the chosen inside diameter $d_i$ according to techniques well known to those skilled in the art, the circuit of electrode 18 can be placed into self-resonance.

Figure 11:
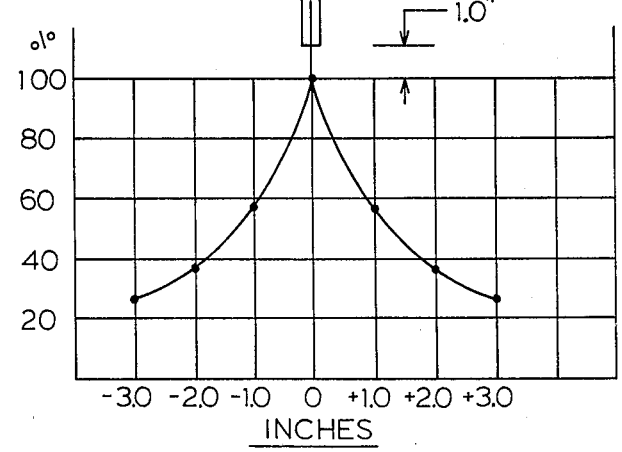
FIG. 11 is a graph showing the relative power density of the electrode of the present invention with respect to distance normal to the plane of the electrode.

Referring now to FIG. 11, the tested performance of an electrode according to the FIGS. 4 and 5 embodiment of the present invention is shown. In that electrode, semi-annular disk members 20 were formed of sheet aluminum having an outside diameter $d_o$ of 20 inches and an inside diameter $d_i$ of 10 inches. The dielectric material 22 comprised polytetraflourethylene of 0.020 inches in thickness. The total thickness of the tested electrode including a dielectric covering over the entire electrode for esthetic reasons was less than 1.0 inches. The relative power level is referenced to a point in the plane 1.0 inch from the inside electrode edge. The energy on either side of the plane of the electrode 18 dropped off rapidly being almost 50% diminished at a distance of one inch from the plane of the electrode 18.

While the preferred embodiment as hereinbefore described is constructed with two pairs of semi-annular conductive disk segments 20 with short arc-length members 21, other embodiments are possible.

As the diameter of the electrode is reduced, the capacity required for resonance increases. Likewise, as the power capability increases, the dielectric thickness also increases. These two factors make it necessary to increase the length of the overlap. This is shown in FIGS. 6–9 with members 20 maintained as semi-annular in shape. In the embodiment of FIGS. 6–7, members 21' have an arc-length of about 90° and, therefore, provide about 50% overlap of members 20. In FIGS. 8–9, members 21" are also just short of being semi-annular, thus providing virtually 100% overlap. Note, however, that the increased overlap has not changed the current path length nor the inductance, thus confirming that the electrodes 18' and 18" of FIGS. 6–9 represent a single turn resonant device.

Any number of overlapping disk segments 20, 21 can be employed as long as a resonant condition is maintained. For example, FIG. 12 shows an electrode 18''' employing two sets of three partial annular disk segments 20', 21''' of about 120° arc each, disposed on either side of an annular disk of dielectric material 22'''. In a similar manner, FIG. 13 shows an electrode 18'''' employing two sets of four partial annular disk segments 20'', 21'''' of about 90° arc each, disposed on either side of an annular disk of dielectric material 22.

Note that in the various embodiments as herein described, as the number of disk segments 20, 21 increases, each individual capcitance value also increases. Thus, there is a practical limit as to available area for the capacitances. Conductive disk segments can, of course, be stacked, where multiple dielectric layers are used, to obtain the capacitance desired without materially modifying the inductance value. If smaller conductive disk segments are used, more of them are required and, obviously, there would be more than four overlapping capacitors. Likewise, fewer than four can be used as long as the total series capacitance resonsates the inductance.

Wherefore, it can be seen that the electrode of the present invention has truly achieved its objective of producing an energy pattern concentrating the majority of the energy within the plane and area internal to the electrode.

Having thus described my invention, I claim:

1. In an electrode for use in the treatment of animal tissue by hyperthermia comprising electrically conductive material disposed to form a single-turn self-resonant loop including means for coupling to a supply of medically assigned radio frequency energy, the improvement comprising:

the electrically conductive material comprising a plurality of planar members being shaped in the form of partial annular disk segments, said members being disposed in overlapping spaced relationship with a dielectric material disposed between overlapping portions to form an annular disk electrodes which is self-resonant at the medical frequency.

2. In an electrode for use in the treatment of animal tissue by hyperthermia comprising electrically conductive material disposed to form a single-turn self-resonant loop including means for coupling to a supply of medically assigned radio frequency energy, the improvement comprising:

the electrically conductive material comprising a plurality of planar members being shaped in the form of partial annular disk segments, said members being disposed, in spaced end-to-end relationship to form a pair of annular, disks, said annular disks being disposed in close adjacent, spaced, relationship with a dielectric material disposed therebetween and having said members of one said disk covering the space between adjacent members of the other of said disks to form an annular disk electrode which is self-resonant at the medical frequency.

3. An electrode for use in the treatment of animal tissue by hyperthermia wherein a planar field of energy is required, the electrode comprising;:
   (a) an anular disk of dielectric material having an outside diameter $d_o$ and an inside diameter $d_i$;
   (b) a first pair of semi-annular disk members of electrically conductive material having an outside radius $d_o/2$ and inside radius $d_i/2$ disposed against one surface of said annular disk in end-to-end spaced relationship;
   (c) a second pair of semi-annular disk members of electrically conductive material having an outside radius $d_o/2$ and an inside radius $d_i/2$ disposed against the other surface of said annular disk in end-to-end spaced relationship and rotated 90° with respect to said first pair of semi-annular disk members to form an annular disk electrode self-resonant at medically assigned frequencies; and,
   (d) means operably connected to the electrode for coupling radio frequency energy to said disk members.

4. An electrode for use in the treatment of animal tissue by hyperthermia wherein a planar field of energy is required, the electrode comprising:
   (a) an annular disk having an outside diameter $d_o$ and an inside diameter $d_i$, said annular disk comprising a plurality of overlapped partial annular electrically conducting plate members having an outside radius of $d_o/2$ and an inside radius of $d_i/2$, said overlapped conducting plate members having a dielectric material disposed between overlapping portions to form capacities, said overlaps being an amount such that for the number of said members, the spacing therebetween, and said dielectric material the capacities in combination with the inductance determined by $d_o$ and $d_i$ will make the electrode substantially self-resonant at medically assigned frequencies; and,
   (b) means operably connected to said disk for coupling radio-frequency energy thereto.

* * * * *